United States Patent [19]
Budyko et al.

[11] Patent Number: 4,945,910
[45] Date of Patent: Aug. 7, 1990

[54] DEVICE FOR ELECTROANALGESIA OF PATIENT'S TISSUES

[76] Inventors: Viktor A. Budyko, ulitsa Mira, 20, Kv. 60; Vladimir V. Konovalenko, ulitsa Vodonapornaya, 16a; Andrei F. Ivanchenko, ulitsa Angolenko, 14a, kv. 17; Valentin D. Kutsov, ulitsa Kedrovaya, 67; Boris N. Lastochkin, prospekt Lenina, 58, kv. 4; Vladimir M. Krokhmal, prospekt 40 let Pobedy, 51, kv. 135; Nikolai N. Zhdan, ulitsa Sytova, 2, kv. 32, all of, Zaporozhie, U.S.S.R.

[21] Appl. No.: 283,366
[22] PCT Filed: Feb. 25, 1988
[86] PCT No.: PCT/SU88/00045
    § 371 Date: Nov. 2, 1988
    § 102(e) Date: Nov. 2, 1988
[87] PCT Pub. No.: WO88/06906
    PCT Pub. Date: Sep. 22, 1988

[30] Foreign Application Priority Data
    Mar. 17, 1987 [SU] U.S.S.R. .............................. 4211982

[51] Int. Cl.$^5$ .............................................. A61N 1/34
[52] U.S. Cl. ................................................... 128/421
[58] Field of Search ............... 128/419 R, 420 R, 421, 128/422

[56] References Cited
U.S. PATENT DOCUMENTS
3,955,583  5/1976  Horauf ........................... 128/420 R
4,301,794 11/1981  Tapper ........................... 128/419 R
4,372,319  2/1983  Ichinomiya et al. ............. 128/421

*Primary Examiner*—Lee S. Cohen
*Attorney, Agent, or Firm*—Ladas & Parry

[57] ABSTRACT

A device for electroanalgesia of patients' tissues comprises series connected a generator (1) of asymmetric pulses some of which at the generator output have longer duration so as to provide electroanalgesia of the patient's tissues, while other pulses have shorter duration so as to provide depolarization of the patient's tissues, a current regulator (2) and a current stabilizer (3) to which are connected electrodes (4, 5) for connection directly to the patient and to a means for exerting a therapeutic effect upon the patient. Connected to one of the electrodes (4, 5) is the input of a pulse shaper unit (6) adapted to produce a pulse in response to the closure of the electric circuit of the electrodes through the patient's tissues, while the output of said pulse shaper unit is connected to the input of a trigger unit (7) of the generator of asymmetric pulses adapted to initiate the generator from a shorter-duration pulse, the output of said trigger unit being connected to the input of the generator (1) of asymmetric pulses.

7 Claims, 1 Drawing Sheet

DEVICE FOR ELECTROANALGESIA OF PATIENT'S TISSUES

TECHNICAL FIELD

The invention relates to medical engineering and more specifically to a device for electroanalgesia of patients' tissues.

PRIOR ART

At present both medicamental and physical methods of dental anesthesia are used for preparing dental tissues. Since medicamental methods may inflict allergic reactions upon patients, it is physical methods that are most promising in this field, which are based on the use of direct electric current which when passed through the dental tissues to be prepared causes a local anesthetic effect. However, when flowing through the dental tissues direct electric current causes polarization of these tissues, resulting in a loss of the anesthetic effect. Restoration of this effect is attained by virture of depolarization of the dental tissues which is effected by a transient passing of electric current in the reverse direction. Further development of electroanalgesia equipment based on the use of electric current is aimed at increasing the anesthetic effect.

One state-of-the-art electroanalgesia apparatus for preparing hard dental tissues is known to comprise series-connected a direct current regulator, a direct current stabilizer and a direct current polarity reversal switch made as a toggle switch, as well as electrodes for connection directly to patient's body and to a means exerting therapeutic effect upon the patient and to the direct current polarity reversal switch, one of said electrode being essentially a clip fitted on, e.g., the lobule of the patient's ear, while the other is in fact a clamp fixed in the handpiece of a dental engine.

To effect electroanalgesia of the hard dental tissues during their preparation the direct current polarity reversal switch is set by the surgeon to a position, wherein a negative potential is applied to the chip-electrode, while a positive potential is impressed upon the other electrode. Upon closing an electric circuit of the electrodes through the hard dental tissues an anesthetic effect is observed, accompanied also by polarization of the tissues involoved. The tissue polarization process affects adversely the anesthetic effect and results in painful sensations felt by the patient. Patient's response to arising pain serves as a signal to the surgeon to cease tooth preparation, reverse the polarity toggle switch and the following transient closing of the electrodes without tooth preparing so as to depolarize the hard dental tissues. After depolarization the surgeon sets the polarity toggle switch to effect electroanalgesia and resumes the tooth preparation procedure.

It ensures from the foregoing discussion that despite the polarizatin of the hard dental tissues the local anesthesia apparatus mentioned above fails to eliminate completely the painful sensations felt by the patient and caused by polarization of the hard dental tissues, since depolarization is carried out in said apparatus by the surgeon just against the patient's painful sensation.

One more prior-art device for electroanalgesia of patients' tissues is known to comprise series-connected generator of asymmetric pulses wherein some of its pulses at the generator output have greater duration to provide electroanalgesia of patient's tissues accompanied by their polarization, while other pulses have shorter duration so to depolarize the patient's tissues, a current regulator and a current stabilizer to which are connected electrodes for a direct connection to the patient and to a means exerting an analgesic effect upon the patient.

In the device discussed above operation of the generator of asymmetric pulses occurs no matter whether the electric circuit of the electrodes closes through the patient's tissues or not. That is why the starting of the pulse generator produced upon closing the electric circuit of the electrodes may have any polarity.

The device described above is employed for treatment of patients tending to drug addiction, as well as of those suffering from asthma, insomnia, and facial paralysis. Besides, the device is applicable for the purpose of analgesia and anesthesia. However, use of the device is of little avail in preventive stomatology for preparation of hard dental tissues accompanied by frequent short-time losses of electric contact between the dental engine and the tooth being treated, since it might result in that only the pulses of larger duration will act upon the hard dental tissues, thus producing an electroanalgesic effect thereon, whereas the action of shorter-duration pulses that provide for tissue depolarization will be time-coincident with a loss of electric contact between the dental engine and the tooth involved. As the relative symmetric pulse duration increases, such a time coincidence happens to be more probable.

If follows from all the foregoing that the device for electroanalgesia of patient's tissues though producing electric pulses for depolarization of the tissues involved but fails to assure their effect on the patient's hard dental tissues, with the result that the patient may have painful sensations caused by polarization.

DISCLOSURE OF THE INVENTION

The invention has for its principal object to provide a device for electroanalgesia of patient's tissues, wherein patient's painful sensations caused by polarization of the hard dental tissues are decreased by virture of depolarization of the patient's hard dental tissues carried out periodically and synchronously with each closure of the electric circuit of the electrodes through said tissues.

The foregoing object is accomplished due to the fact that a device for electroanalgesia of patients' tissues, comprising series-connected a generator of asymmetric pulses some of which at the generator output having longer duration to provide electroanalgesia of patients' tissues accompanied by their polarization, while other pulses produced by the generator have shorter duration to provide depolarization of patients' tissues, a current regulator and a current stabilizer to which are connected electrodes for direct connection to the patient and to a means exerting a therapeutic effect upon the patient, according to the invention, comprises also series-connected a pulse shaper unit adapted to produce a pulse in response to the closure of the electric circuit of the electrodes through the patient's tissues, the input of said pulse shaper unit being connected to one of the electrodes, and a trigger unit of the generator of asymmetric pulses adapted to initiate the generator from a shorter-duration pulse, said trigger unit being connected through its output to the input of the generator of asymmetric pulses.

It is expedient that in the device for electroanalgesia of patients' tissues the pulse shaper unit adapted to produce a pulse in response to the closure of the electric circuit of the electrodes through the patients' tissues be made as a comparator.

Provision of a series-connected pulse shaper unit adapted to produce a pulse in response to the closure of the electric circuit of the electrodes through the patient's tissues, whose input is connected to one of the electrodes, and a trigger unit of the generator of asymmetric pulses adapted to initiate the generator from a shorter-duration pulse, whose output is connected to the input of the generator of asymmetric pulses, ensures tha a due action is produced upon the patient's hard dental tissues by a pulse effecting depolarization in cases of any time intervals in the tooth preparation procedure accompanied by a loss of electric contact between the dental engine and the tooth involved, thus restoring the analgesic effect lost due to tissue polarization and hence adds to the efficiency of anesthesia.

Embodiment of the pulse shaper unit adapted to produce a pulse in response to the closure of the electrode circuit through the patient's tissues in the form of a comparator increases the depolarization rate of the device, which adds also to the efficiency of anesthesia.

SUMMARY OF THE DRAWINGS

In what follows the invention will become more apparent from a detailed description of a specific embodiment thereof to be read with reference to the accompanying drawings wherein:

FIG. 3 is a time chart of asymmetric current pulses produced in response to the closure of the electrode electric circuit through the patient's tissues.

PREFERRED EMBODIMENT OF THE INVENTION

Figure 1:
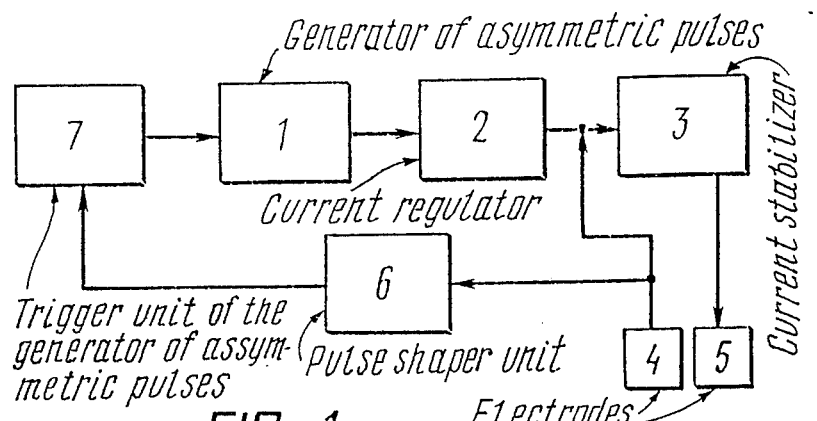
FIG. 1 is a block diagram of a device for electroanalgesia of patients' tissues, according to the invention.

The device for electroanalgesia of patients' tissues comprises a generator 1 (FIG. 1) of asymmetric pulses, some of said pulses at the output of said generator having longer duration so as to provide electroanalgesia of a patient's tissues accompanied by their polarization, while other pulses produced by said generator have shorter duration so as to provide depolarization of the patient's tissues. The output of said generator is connected to the input of a current regulator 2 whose output is connected to the input of a current stabilizer 3. Connected to said input and said output of the current stabilizer 3 are respective electrodes 4, 5 adapted for connection directly to the patient and to a means exerting therapeutic effect upon the patient. The device incorporates also a pulse shaper unit 6 adapted to produce a pulse in response to the closure of the electrode circuit through the patient's tissues, the input of said pulse shaper unit being connected to one of the electrodes, e.g., to the electrode 4, and a trigger unit 7 of the generator of asymmetric pulses adapted to initiate the generator from a shorter-duraction pulse, the input of said trigger unit being connected to the output of the pulse shaper unit 6, while its output is connected to the input of the generator 1 of asymmetric pulses.

Figure 2:
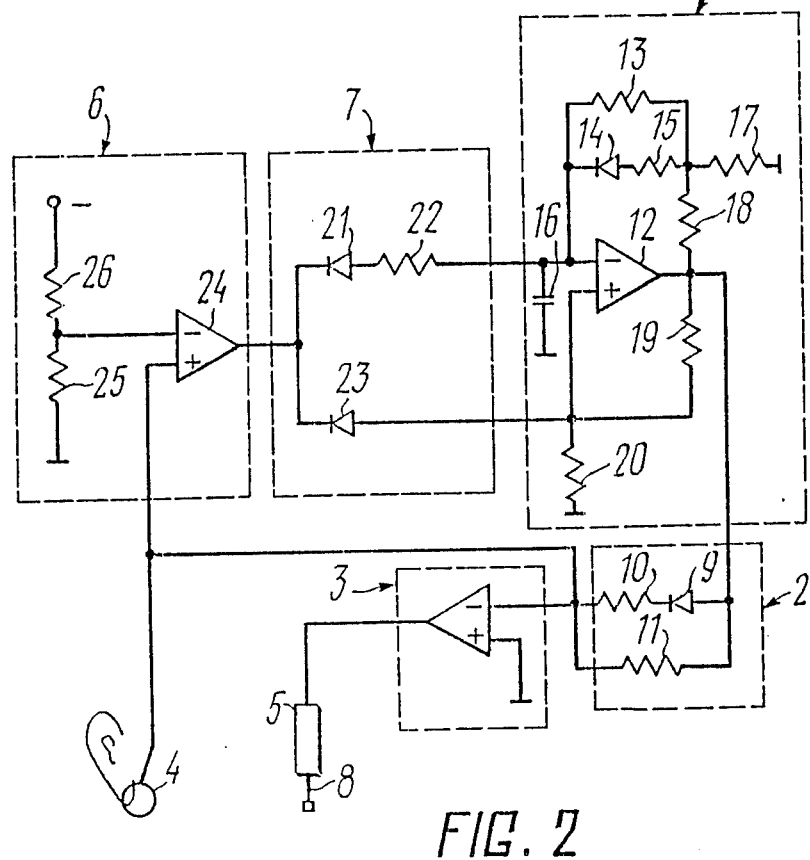
FIG. 2 is a schematic circuit diagram of a device for electroanalgesia of patients' tissues, incorporating a comparator as a pulse shaper unit adapted to produce a pulse in response to the closure of the electrode circuit through the patient's tissues, according to the invention.

The herein-proposed device for electroanalgesia of patients' tissues is adapted for use in preparation of the hard dental tissues. Accordingly, it is a dental engine which is used as a means for exerting a therapeutic effect upon the patient. The electrode 5 is made as a clamp fixed in a handpiece 8 (FIG. 2) of the dental engine, while the electrode 4 is shaped as a clip fastened on the patient's auricle lobule.

In the embodiment of the device described herein the current stabilizer 3 is in fact a controlled bipolar inverting current source with a floating load, built around an operational amplifier whose output is connected to the electrode 5 which is connected to the dental engine handpiece 8. The noninverting input of the stabilizer 3 is earthed, and the electrode 4 is connected to the inverting input of the stabilizer. The current regulator 2 is built around series-connected a diode 9 and a resistor 10, a resistor 11 being connected parallel to both.

To promote understanding of the operation of the device for electroanalgesia of patients' tissues, FIG. 3 presents a time chart of asymmetric current pulses produced in response to the closure of the electrode electric circuit through the patient's tissues, wherein time 't' is plotted against the axis of abscissas and current $I_a$ that provides for electroanalgesia of the patient's tissues is plotted against the axis of ordinates, as well as current $I_d$ that provides for depolarizatin of the patient's tissues.

The valve of resistance offered by the resistor 11 (FIG. 2) depends on the intensity of the electroanalgesia current $I_a$ (FIG. 3), while the value of resistance offered by the resistor 10 (FIG. 2) depends on the depolarization current $I_g$ (FIG. 3), the latter current being in excess of the electroanalgesia current $I_a$ due to the parallel connection of said resistor 10 (FIG. 11) and said resistor 11. The diode 9 is coupled to the inverting input of said operational amplifier through the resistor 10.

In the embodiment of the device described herein the generator 1 of asymmetric pulses is in fact a controlled bipolar one built around an operational amplifier 12. Asymmetry of the positive and negative pulses is attained due to insertion in the negative feed-back circuit of the operational amplifier 12 of series-connected a diode 14 and a resistor 15, both being connected in parallel to a resistor 13. The diode 14 is connected to the inverting input of the operational amplifier 12 with its cathode. Duration of the negative pulses at the output of the operational amplifier 12 is dependent largely upon the value of the resistor 13 and the capacity of a capacitor 16 connected to the inverting input of the operational amplifier 12, while duration of the positive pulses is a function of the value of the resistor 15 and capacity of the capacitor 16. Duration of asymmertic pulses produced by the generator 1 and hence that of the electroanalgesia and depolaration is controlled by varying the ratio between the values of the resistors 13 and 15.

The generator 1 of asymmetric pulses comprises also resistors 17, 18 which establish a voltage divider aimed at elimination of spurious generation that may arise in cases where the output voltage of the generator 1 of asymmetric pulses exceeds the output voltage of the trigger unit 6 adapted to intitate the generator of asymmetric pulses from a shorter-duration pulse, and resistors 19, 20 which establish a positive feed back circuit of the operational amplifier 12. The capacitor 16 and the resistors 17, 20 are earthed, the resistors 18, 19 are connected to the output of the operational amplifier 12, the resistor 20, 19 are connected to the noninverting input of the operational amplifier 12, and the resistors 17, 18 are connected to the junction point of the resistors 13 and 15.

The trigger unit of the generator of asymmetric pulses adapted to initiate the generator from a shorter-duration pulse in the given particular embodiment of the device comprises a diode 21, a resistor 22 and a diode 23 which serves in combination with the diode 21 for isolation of the inputs of the operational amplifier 12. The cathodes of the diodes 21, 23 are tied together and serve as the input of the trigger unit 7 of the generator of asymetric pulses adapted to initiate the generator from a shorter-duration pulse. The anode of the diode 23 is connected to the noninverting input of the operational amplifier 12, and the anode of the diode 21 is connected to the resistor 22 which in turn is connected to the inverting input of the operational amplifier 12.

The pulse shaper unit 6 adapted to produce a pulse in response to the closure of the electrode circuit through the patient's tissues is made in this particular embodiment of the device as a comparator 24 built around an operational amplifier. Reference voltage across the inverting input of the comparator 24 is set by the voltage divider built around resistors 25, 26. The resistor 25 is earthed, while the resistor 26 is connected to the negative pole of the supply source.

The operational amplifier 12, the comparator 24 and the current stabilizer 3 are fed from a bipolar supply source (omitted in the Drawing).

The device for electroanalgesia of patients' tissues operates as follows.

The electric circuit of the electrode 5 (FIG. 1) fixed in the handpiece 8 (FIG. 2) of the dental engine and that of the electrode 4 secured on the patient's auricle lobule are closed as soon as the electrode 5 (FIG. 1) contacts the patient's tooth being treated. A voltage approximating zero is set across the input of the comparator 24, which is in fact the noninverting input of the operational amplifier, while a positive voltage is set across the output of the comparator 24. The diode 21 of the trigger unit 7 adapted to initiate the generator of asymmetric pulses from a shorter-duration pulse and the diode 23 are disabled, while the capacitor 16 is recharged through the resistor 13, the diode 14, the resistor 15 and the resistor 18 so that a shortduration positive pulse is shaped at the output of the operational amplifier 12 of the generator 1 of asymmetric pulses. The positive pulse thus formed passes along the circuit of the diode 9 and the resistors 10, 11 of the current regulator 2 and shapes a shorter-duration negative pulse at the output of the operational amplifier serving as the current stabilizer 3 so as to provide depolarization of the patient's tissues, i.e., the hard dental tissues. Duration $\tau$ (FIG. 3) of such pulses and the intensity of the current $I_g$ determine the depolarization procedure which starts at the instant of each closure of the circuits of the electrode 4 (FIG. 2) and the electrode 5 through the patient's tissues. The duration $\tau$ is set within 5 and 150 ms, and the intensity of the current $I_g$, within 80 and 150 $\mu$A.

The depolarization procedure is followed by the electroanalgesia procedure which is established by longer-duration pulses, the intensity of the electroanalgesia current $I_a$ (FIG. 3) depends solely on the value of the resistor 11 (FIG. 2) of the current regulator 2, while duration of electroanalgesia depends on the capacity of the capacitor 16 and the resistance value of the resistors 13, 18, 19, 20 of the generator 1. Duration of these pulses is set within 3 to 5 s and the intensity of the current $I_a$ within 30 to 100 $\mu$A.

When the time $t_1$ (FIG. 3), $t_2$ spent for the tooth preparation is less than the oscillation period T of the generator 1 (FIG. 2) of asymmetric pulses, the depolarization procedure is not set repeatedly. Should however the time $t_3$ (FIG. 3) spent for the tooth preparation exceed said period T the depolarization procedure resumes automatically. In cases of any interruptions in the tooth preparation procedure shown in FIG. 3 as intervals $t_4$, $t_5$ there is assured an action upon the hard dental tissues by current pulses that provide for depolarization which diminishes painful sensations in the patient caused by polarization of the hard dental tissues and hence adds to the efficiency of analgesia.

The herein-proposed device for electroanalgesia of patients' tissues have been trialled clinically on patients given preventive stomatological treatment in cases of noncomplicated surface, middle and deep caries, especially pericervical one, in opening the pulp cavity and amputation of the coronal pulp in cases of acute or chronical pulpitis. For all patients treated the electroanalgesia current was 60 $\mu$A, the depolarization current, 100 $\mu$A, duration of an electroanalgesia current pulse, 5 s, duration of a depolarization current pulse, 50 ms.

The control group incorporated 100 patients, males and females aged from 10 to 59. Efficiency of the analgesic effect was established by inquiring the patients upon completing the preparation of the hard dental tissues. In forty patients the device was periodically put out of operation in the course of preparation of the hard dental tissues, with the result that thirty eight patients started feeling painful sensations. It has been noted that in the case of deep and pericervical caries complete and partial analgesia is observed in 95 percent of cases, and in the cases of surface caires, in 88 percent of cases. No analgesic effect was noted in five patients aged from 41 to 57. It has also been established that in advanced-aged patients a complete analgesic effect is observed much less frequenty than in middle-age persons and especially in young patients. It was found that the same patient exhibited the analgesic effect and the absence of that in the course of preparation of different teeth.

Complete or partial analgesia in the course of opening the pulp cavity and amputation of the coronal pulp in acute and chronic pulpitis was observed in 91 percent l of cases.

It has been found that the device gives no side effects and has contraindications for use.

Industrial Application

The invention can be used to good advantatge in preventive stomatology for preparing hard dental tissues involved in treatment of uncomplicated surface, middle and deep caries, especially pericervical one, as well as in opening the pulp cavity and amputation of the coronal pulp in cases of acute or chronical pulpits. The invention will find most utility when applied in children's stomatology.

We claim:

1. A device for electroanalgesia of a patient's dental tissues comprising an electrode to be connected directly to the patient and an electrode for intermittent electrical connection to the patient's tooth, and a pulse train generator connected to said electrodes for transmitting a train of current pulses between said electrodes when an electric circuit is closed between said electrodes through the patient's tissues, said pulse train comprising a series of alternating first and second current pulses, said current pulses being positive and of a first duration and said second current pulses being negative and of a second duration shorter than said first duration, and pulse triggering means effective upon a closure of said electric circuit, after an opening thereof, for re-transmitting said pulse train starting always with one of said second pulses.

2. A device as claimed in claim 1 wherein said first current pulses have an amplitude of 30 to 100 µA and a duration of 3 to 5 seconds.

3. A device as claimed in claim 1, wherein said second current pulses have an amplitude of 80 to 150 µA and a duration of 5 to 150 milliseconds.

4. A device as claimed in claim 1, wherein said pulse train generator comprises a series connected circuit of the following units in the named order, the output of each unit serving as the input of the unit successive thereto: an asymmetric pulse generator for generating current pulses of a first duration and current pulses of a second duration shorter than said first duration, a current regulator for controlling the amplitude of said pulses, a pulse shaper for producing a pulse in response to the closure of said electric circuit, and a trigger for causing said asymmetric generator to immediately generate a train of pulses starting with pulses of said second duration, said pulse train generator including a current stabilizer the input of which is an output from said current regulator, the input to and the output from said current stabilizer being each connected to a differnt one of said electrodes.

5. A device as claimed in claim 4, wherein the current stabilizer comprises an operational amplifier in the form of a controllable bipolar floating load inverting current source.

6. A device as claimed in claim 4, wherein the asymmetric pulse generator cmprises an operational amplifier and is of a controllable bipolary type.

7. A device as claimed in claim 4, wherein the pulse shaper, comprises an operational amplifier in the form of a comparator.

* * * * *